(12) United States Patent
Alzner

(10) Patent No.: US 6,747,451 B2
(45) Date of Patent: Jun. 8, 2004

(54) METHOD FOR AVOIDING OVER-CONVOLUTIONS IN THE PHASE CODING DIRECTION IN NUCLEAR MAGNETIC RESONANCE TOMOGRAPHY

(75) Inventor: Andreas Alzner, Hemhofen (DE)

(73) Assignee: Siemens Aktiengesellschaft, München (DE)

( * ) Notice: Subject to any disclaimer, the term of this patent is extended or adjusted under 35 U.S.C. 154(b) by 137 days.

(21) Appl. No.: 10/128,169

(22) Filed: Apr. 22, 2002

(65) Prior Publication Data

US 2002/0173716 A1 Nov. 21, 2002

(30) Foreign Application Priority Data

Apr. 23, 2001 (DE) .......................... 101 19 785

(51) Int. Cl.⁷ ................................ G01V 3/00
(52) U.S. Cl. ...................... 324/307; 324/309
(58) Field of Search .................. 324/307, 309, 324/311, 314, 318; 375/279; 364/414

(56) References Cited

U.S. PATENT DOCUMENTS 4,606,004 A * 8/1986 Crawford et al. ........... 382/280
6,304,614 B1 * 10/2001 Abbaszadeh et al. ....... 375/279

* cited by examiner

*Primary Examiner*—Brij B Shrivastav
(74) *Attorney, Agent, or Firm*—Schiff Hardin LLP

(57) ABSTRACT

In a method and magnetic tomography apparatus wherein over-convolutions in the phase coding direction in magnetic resonance tomography are avoided, orthogonal slices are measured as overview presentations (localizers) in a first step and slices for the following measurement series are then determined. Overlapping phases and the magnitude of the appertaining signal are calculated and a warning is emitted when this over-convoluted signal exceeds a reference value. A selection possibility is then offered for reducing the phase coding steps and enlarging the field of view and, if selected, the phase coding step width is automatically reduced.

8 Claims, 2 Drawing Sheets

METHOD FOR AVOIDING OVER-CONVOLUTIONS IN THE PHASE CODING DIRECTION IN NUCLEAR MAGNETIC RESONANCE TOMOGRAPHY

BACKGROUND OF THE INVENTION

1. Field of the Invention

The present invention is directed in general to a method for avoiding over-convolutions in the phase coding direction in magnetic resonance tomography employing surface coils. In particular, the present invention is directed to a method of avoiding over-convolutions by adaptation of the parameters of a magnetic resonance examination to be undertaken, so that such over-convolutions do not occur or occur only to an innocuous extent.

2. Description of the Prior Art

Magnetic resonance tomography is a tomogram method for medical diagnostics that makes it possible to show structures of the human body to a significant extent and in detail. In principle, magnetic resonance tomography is based on the application of a strong external magnetic field in a region of a subject to be examined, causing a certain portion of the magnetic spins of the nuclei to align. More precisely, a statistically defined number of nuclear spins assumes specific energy levels. When a radio-frequency pulse supplies additional energy at a resonant frequency that is substance-specific and is dependent on the gyromagnetic constant, a specific number of nuclear spins assumes different energy levels. After the radio-frequency pulse is deactivated, the return onto the original energy levels can be measured in the external magnetic field by receiving the energy emitted at the resonant frequency.

In practical application, it is usually the distribution of the hydrogen in the human body that is measured, since, a good presentation of the tissue is established merely by detecting the hydrogen distribution due to its widespread nature within the human body in all tissues, and hydrogen can be detected especially well on the basis of its high gyromagnetic constant.

It is necessary for magnetic resonance tomography that the signal of a nuclear spin, referred to below as an MR signal, be able to be assigned to location information. A number of detailed methods are known for this purpose, including the use of combinations of additionally activated magnetic fields, excitation frequencies and readout times at the resonant frequencies. Fundamentally, the physical effect is always utilized that the resonant frequency of an MR signal in an external magnetic field is location-dependent when this external magnetic field no longer has a constant field strength, but changes over a distance, as is the case, for example, given an additionally applied, linearly rising or dropping magnetic field. Such a magnetic field is referred to as gradient magnetic field. Further, such a different field also causes various nuclear spins that initially resonate with the same phase position to diverge in phase after a certain time, and to retain this phase difference when the additional magnetic field is deactivated after a certain time and they again resonate with the same resonant frequency. This is the basic principle of phase coding.

A radio-frequency pulse at the resonance frequency of the nuclear spins in the basic magnetic field first excites the nuclear spins, and the overall magnetic moment of the nuclear spins is partially and entirely rotated (is referred to as 90° excitation) into the plane perpendicular to the basic magnetic field. The magnetization vectors distributed in the measurement volume thereby essentially exhibit an identical phase after the excitation. Subsequently, two magnetic gradient fields are activated in two evaluation directions, referred to as the phase coding gradient and the frequency coding gradient. These magnetic field gradients have a linear course. Consequently, the resonant frequency and phase of the individual magnetization vectors are dependent on the location. The magnetic field is activated for a fixed, defined time t. When the phase coding gradient is in turn deactivated, then the phases of the nuclear spins have become different from each other in location-dependent fashion. This setting of the phases is preserved until the readout time. When the radio frequency resonance signal that the nuclear spins emit when they drop back from their excitation level into the basic level is received, then the phase position of the individual nuclear spins can be interpreted by mathematical methods, for example Fourier methods, and a location in the phase coding direction can be allocated to the phase. In phase coding, this switching is multiply implemented—for example, 256 times—with different amplitudes. A different phase coding gradient having a higher value is thereby added at every repetition of the above-described method. The individual steps of the phase coding gradient usually exhibit an equidistant spacing.

The above-described, additional magnetic fields or gradient fields are generated by two coils that each generate a magnetic field, these fields being oppositely directed. A magnetic field arises in the volume element between the two coils that increases or decreases linearly over distance. The nuclear spins are excited by a radio-frequency excitation coils and the MR signal is received via the same coils or specific reception coils. Such specific reception coils are small, additional coils that, differing from the gradient evaluation coils, the basic magnetic field coil and the large radio frequency transmission/reception coil, are permanently installed in the nuclear magnetic resonance tomography apparatus. The reception coils are relatively small and compact and usually are flat and can be placed in the proximity of the organ to be examined. These specific reception coils are also referred to as surface coils.

In an examination with surface coils or with the large transmission/reception coil, the problem known as over-convolution can occur in the phase coding direction. It can occur in a phase coding method that a nuclear spin cannot be unambiguously topically assigned because a nuclear spin close to the middle of the coils in the region of a small gradient exhibits the same phase as a nuclear spin outside a selected field of view (FOV) in the region of a high gradient that has additionally rotated at least one full period of $2\pi$. This case fundamentally occurs when the FOV is smaller in the phase coding direction than the subject under examination. Dependent on the number and size of the selected surface coils, these receive signals not only from the FOV but also from sections of the examination subject that lie farther away. Since a gradient field can still be noticed in these regions lying outside the field of view and a reception by the surface coil from these regions cannot be completely prevented, it can occur that the signals from this region exhibit the same phase as the signals from the actual field of view, and are no longer negligibly small, so that disturbances in the form of superimpositions thus occur. This particularly occurs given the employment of surface coils that are intended to represent only a small region in great detail and where large regions of the body of the person to be examined lie outside the actual field of view.

SUMMARY OF THE INVENTION

It is an object of the present invention to provide a method and an apparatus which avoid disturbing over-convolutions in magnetic resonance tomography, particularly MR imaging with surface coils.

This object is inventively achieved in a method according to the invention for avoiding over convolutions in the phase coding direction in magnetic resonance tomography, wherein at least orthogonal slices are measured, or a three-dimensional volume is measured, as an overview presentation in a first step. Slices for the following series of measurements then can be defined in the overview presentation, which are also referred to as localizers. In a further step, a calculation is made to identify overlapping phases and the amount of the appertaining signal is defined, this being a noise signal. If an over-convoluted signal theoretically derives from these calculations that exceeds a reference value, a warning is emitted and a selection possibility is offered in order to reduce the phase coding step width and to thereby enlarge the correctly analyzed field of view. When the offered selection is accepted by an operator, then an automatic reduction of the phase coding step width ensues in conjunction with a reduction of the spatial resolution in phase coding direction.

Advantageously, the above-described method also makes it possible for a rather an inexperienced operator to avoid such over-convolutions.

In an embodiment, the magnetic resonance tomography exposure ensues using a surface coil.

In a specific examination situation wherein a surface coil is employed, it is considerably easier for the operator of a magnetic resonance tomography apparatus to avoid over-convolutions. Since a surface coil can also receive signals from regions beyond the actual field of view that represent an over-convoluted signal relative to signals in the field of view, over-convolutions occur that are very difficult for inexperienced personnel to handle. Due to the automatic calculation and estimate of the potentially arising over-convolutions and the automatically ensuing indication thereof connected with a corresponding variation of the parameters, the operation of the magnetic resonance tomography apparatus is considerably simplified.

Advantageously, the total number of phase coding steps can be retained.

Although the resolution in the phase coding direction is reduced due to such a method, since the phase coding steps, i.e. the spacing of the gradient field pulses, is reduced and, further, the correctly analyzed field of view is thereby automatically enlarged, the original measuring time is preserved. This is particularly advantageous in measurements wherein a patient should hold his or her breath.

A new rectangular region within a field of view can be selected that should be free of over-convolutions and wherein the method is applied again.

A smaller region to be measured thus can be selected that can be measured free of over-convolution under all circumstances. In particular, the desired, increased resolution nonetheless can be nearly achieved. Due to the renewed application of the method, it is possible to prevent over-convolutions from occurring at least in the smaller, selected field of view.

A magnetic resonance tomography apparatus according to the invention has a control computer that is programmed to execute the above-described inventive method.

This magnetic resonance tomography installation exhibits the same advantages of the method.

DESCRIPTION OF THE PREFERRED EMBODIMENTS

Figure 1:
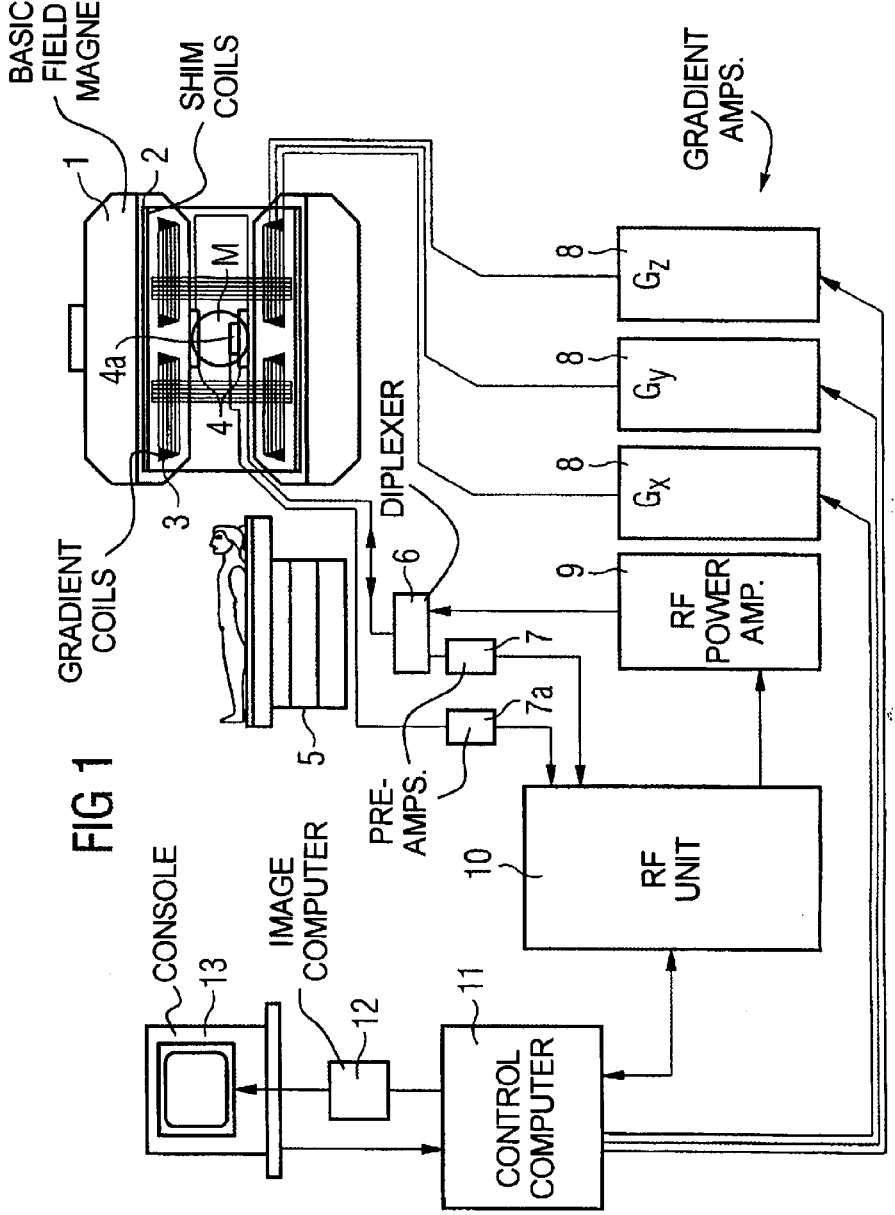
FIG. 1 schematically illustrates a magnetic resonance tomography installation constructed and operating in accordance with the invention.

FIG. 1 is a schematic illustration of a magnetic resonance tomography installation for generating a magnetic resonance image of a subject wherein the inventive method is executed. The structure of this magnetic resonance tomography installation corresponds to that of a conventional nuclear magnetic resonance tomography installation, with the additional features described below. A basic field magnet 1 generates a strong, optimally uniformly fashioned magnetic field for the polarization of the nuclear spins in a measurement volume in the inside of the basic field magnet 1. The high homogeneity of the basic magnetic field required for the magnetic resonance measurement is defined in a spherical measurement volume M into which the parts of the human body to be examined are introduced. This occurs with a displaceable bearing mechanism 5. For the correction of time-invariable influences, shim plates of ferromagnetic material are applied at suitable locations on the basic field magnet 1. Further influences which disturb the uniformity of the basic field magnet are corrected by shim coils 2. A system of cylindrical gradient coils 3 introduced into the basic field magnet 1 serves the purpose of generating linear gradient fields in the three spatial directions or in a Cartesian coordinate system, or some other coordinate system. Each of the three gradient coil systems 3 is supplied with current for generating the gradient magnetic field by an amplifier 8. In the embodiment of a magnetic resonance tomography apparatus shown here, a gradient field is generated in each of the x-direction, y-direction and z-direction. The gradient fields make it possible to topically code the volume to be measured with one of the known pulse sequences.

A radio-frequency antenna 4 is arranged within the gradient coils 3, which converts the radio-frequency pulses emitted by a radio-frequency power amplifier 9 via a transmission/reception diplexer 6 into a magnetic alternating field. Nuclei in the subject are excited by this magnetic alternating field, and the nuclear spins of the subject to be examined or of the region of the subject to be examined are aligned in a rotational motion perpendicular to the basic magnetic field. Likewise, the radio-frequency antenna 4 converts the alternating field emanating from the precessing nuclear spins, i.e. the magnetic resonance signals influenced as a rule by a pulse sequence composed of one or more radio frequency pulses and one or more gradient pulses, into a voltage. This voltage is supplied via the transmission/reception diplexer 6 as well as via a pre-amplifier 7 to a radio frequency unit 10. A narrowly bounded region can be selected with a surface coil 4a, the resonant signals thereof being received and being supplied to the radio frequency reception unit 10 via a pre-amplifier 7a. Such a surface coil 4a usually serves the purpose of obtaining images with especially high resolution and with a good signal-to-noise ratio from a specific organ. A surface coil 4a is thereby usually applied to or on the body of the person to be examined.

A control computer 11 controls the executive sequence of individual measurement sequences; an image computer 12 generates an image from the acquired measured data by means of fast Fourier transformation. The generated image is optically presented to the user at a console 13 that has a keyboard as well as one or more picture screens. The drive of the surface coil 4a also ensues by means of the control computer 11.

Figure 2:
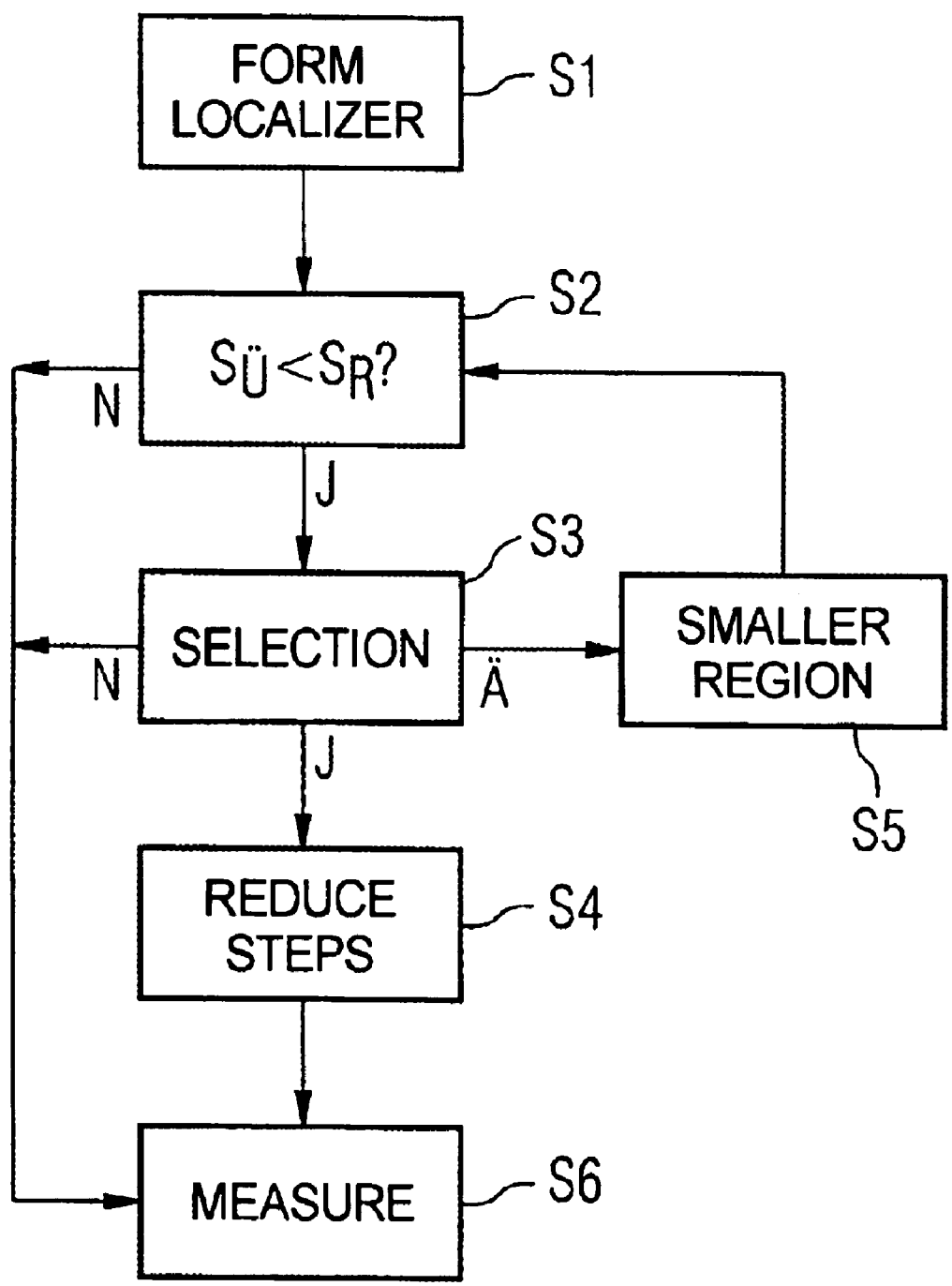
FIG. 2 is a flow chart for the execution of the inventive method in the magnetic resonance tomography installation of FIG. 1.

In a flowchart, FIG. 2 schematically shows an embodiment of the present, inventive method. First, overview exposures (localizers) having a short measurement on time are registered in a first step S1 by the control computer 11 in FIG. 2 using the radio-frequency antenna 4 and are visibly presented to the user on the console 13 by the image computer 12. Usually, three tomograms residing on one another are measured as localizers. When planning the next series, a calculation for a field of view indicated by an operator is then made in a further step S2 in the control computer 11 as to whether an over-convolution signal $S_{\ddot{u}}$ (if present) is smaller then a reference signal $S_R$ for the over-convolution. A reference signal having a magnitude of 3% of the average signal in the field of view is, for example, beneficial. When this is the case, the selected measurement sequence is implemented for the field of view in a step S6, this sequence being implemented by the control computer via the radio frequency antenna 4 or the surface coil 4a. If, however, the reference signal $S_R$ is exceeded, then the operator at the magnetic resonance tomography installation is offered a selection in a next step S3 at the console 13 controlled by the image computer 12, having three decision possibilities. The operator can select changing nothing (represented by the branch M as "no") and can thus have the measurements undertaken immediately in Step S6. It must then be expected that artifacts or mispresentations will occur; however, the operator of the magnetic resonance tomography installation at least was informed thereof in advance. As a second selection possibility (referenced with the branch Y for "yes"), an offer is made to suitably adapt the parameters. This means that the step width is reduced in the phase coding direction, as indicated as step 4 in FIG. 2 that sequences in the control computer 11. As a result of such a reduction of the intervals of the individual phase coding gradients, the correctly analyzed field of view is automatically enlarged in the phase coding direction and the resolution is reduced. The measurement can then again follow in step S6. In Step S3 (represented by the branch M for "modify") the inventive method offers the third alternative of selecting a new, smaller region of the field of view wherein disturbing over-convolutions can be avoided. In a Step S5, a user at the console 13 can more precisely define the smaller region and may undertake even more settings. The method is then iteratively implemented for such a new field of view beginning with the calculation step as to whether an over-convolution signal above a reference value is present.

In the exemplary embodiment described herein, the operator of the magnetic resonance tomography installation thus can select whether the resolution should be reduced to such an extent that over-convolution no longer occurs. This is represented in the flowchart with the branch Y in the step S3. Alternatively, the operator can select that the resolution should be only slightly reduced, and the region free of over-convolution is selected somewhat smaller than the selected field of view. This is represented by the branch M for modify. In particular, it is advantageous that the modifications and parameter settings to be undertaken ensue automated. It is thus also possible for an inexperienced person to produce registrations without disturbing over-convolution artifacts.

Although modifications and changes may be suggested by those skilled in the art, it is in the intention of the inventor to embody within the patent warranted hereon all changes and modifications as reasonably and properly come within the scope of his contribution to the art.

I claim as my invention:

1. A method for avoiding over-convolutions in a phase coding direction in magnetic resonance tomography, comprising the steps of:
   (a) obtaining magnetic resonance data for an overview presentation selected from the group consisting of data for three orthogonal slices of a subject and data for a three-dimensional volume of a subject;
   (b) from said overview presentation, determining slices for a subsequent magnetic resonance measurement sequence which includes phase coding produced by changing a phase coding gradient in phase coding steps each having a step width, said sequence having a field of view associated therewith;
   (c) from the selected slices of said measurement sequence, calculating, in a computer, overlapping phases and a magnitude of a signal produced by said overlapping phases;
   (d) emitting a warning indicating over-convolution if said signal exceeds a reference value;
   (e) together with said warning, offering a selection to a user for reducing said phase coding step width to enlarge said field of view; and
   (f) automatically reducing said phase coding step width if said selection is selected.

2. A method as claimed in claim 1 comprising obtaining said data for said overview presentation and conducting said subsequent magnetic resonance measurement sequence using surface coils.

3. A method as claimed in claim 1 comprising retaining a total number of said phase coding steps when reducing said phase coding step width.

4. A method as claimed in claim 1 comprising, upon emission of said warning in step (d) selecting a rectangular region within said field of view which is designated to be free of over-convolutions, and repeating at least steps (c) and (d) after said rectangular region is selected.

5. A magnetic resonance tomography system, comprising
   a magnetic resonance scanner including a control computer which controls said scanner to obtain magnetic resonance data for an overview presentation selected from the group consisting of data for three orthogonal slices of a subject and data for a three-dimensional volume of a subject;
   said control computer, from said overview presentation, determining slices for a subsequent magnetic resonance measurement sequence by said scanner which includes phase coding produced by changing a phase coding gradient in phase coding steps each having a step width, said sequence having a field of view associated therewith;
   from the selected slices of said measurement sequence, said control computer calculating overlapping phases and a magnitude of a signal produced by said overlapping phases;
   an operator console connected to said control computer, said control computer causing a warning to be emitted at said console, and indicating over-convolution if said signal exceeds a reference value, and together with said warning, to offer a selection to a user for reducing said phase coding step width to enlarge said field of view; and
   said control computer automatically reducing said phase coding step width if said selection is selected via said console.

6. A magnetic resonance tomography system as claimed in claim 5 wherein said scanner includes surface coils and obtains said data for said overview presentation and conducts said subsequent magnetic resonance measurement sequence using said surface coils.

7. A magnetic tomography system as claimed in claim 5 wherein said control computer retains a total number of said phase coding steps when reducing said phase coding step width.

8. A magnetic tomography system as claimed in claim 5 wherein said control computer and said console, upon emission of said warning, allow selection via said console of a rectangular region within said field of view which is designated to be free of over-convolutions, and wherein said control computer, after said rectangular region is selected, again calculates overlapping phases and a magnitude of a further signal produced by said overlapping phases, and causes said console to emit a warning indicating over-convolution if said further signal exceeds said referenced value.

* * * * *